United States Patent [19]

Rainin

[11] Patent Number: 4,490,860
[45] Date of Patent: Jan. 1, 1985

[54] INTRAOCULAR LENS APPARATUS AND METHOD FOR IMPLANTATION OF SAME

[75] Inventor: E. A. Rainin, Danville, Calif.

[73] Assignee: Ioptex Inc., Azusa, Calif.

[21] Appl. No.: 477,028

[22] Filed: Mar. 21, 1983

Related U.S. Application Data

[63] Continuation-in-part of Ser. No. 340,504, Jan. 18, 1982, abandoned.

[51] Int. Cl.³ .................. A61F 1/16; A61F 1/24
[52] U.S. Cl. .................................................. 3/13
[58] Field of Search ........................................ 3/13, 1

[56] References Cited

U.S. PATENT DOCUMENTS

| | | | |
|---|---|---|---|
| 4,159,546 | 7/1979 | Shearing | 3/13 |
| 4,170,043 | 10/1979 | Knight et al. | 3/13 |
| 4,277,852 | 7/1981 | Poler | 3/13 |
| 4,298,994 | 11/1981 | Clayman | 3/13 |
| 4,316,292 | 2/1982 | Alexeev | 3/13 |

Primary Examiner—Ronald L. Frinks
Attorney, Agent, or Firm—Bielen and Peterson

[57] ABSTRACT

An intraocular lens apparatus having an optical lens portion and a mechanism for confining the lens portion within the eye. A marking is applied to the surface of the optical lens portion for indication of a specific zone of the optical lens portion. The marking may consist of an amount of material which is substantially nonreactive to human tissue. The physician is able to align the marking in relation to the pupil of the eye before fixing the optical lens portion within the eye.

8 Claims, 4 Drawing Figures

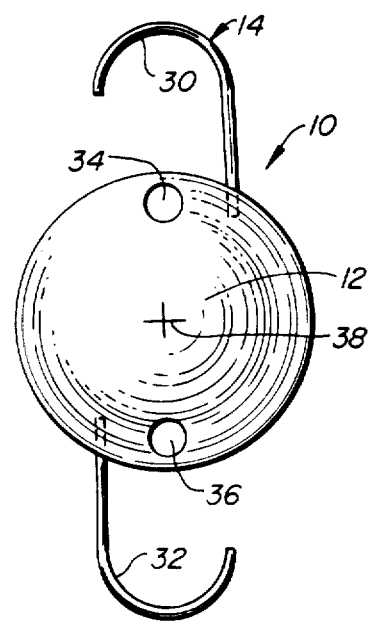
FIG._1.
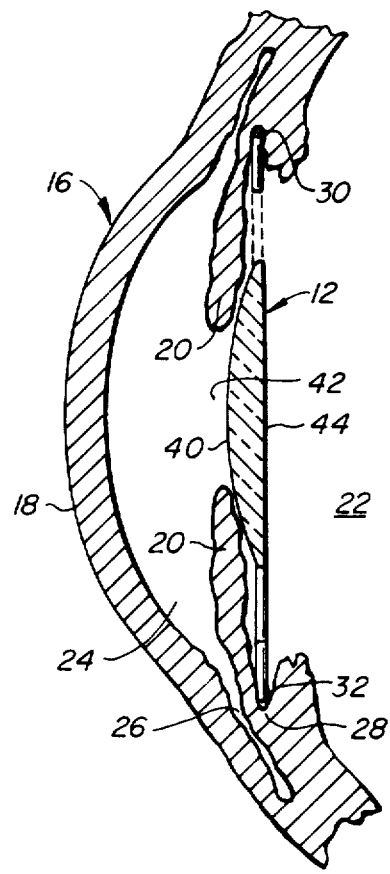
FIG._4.
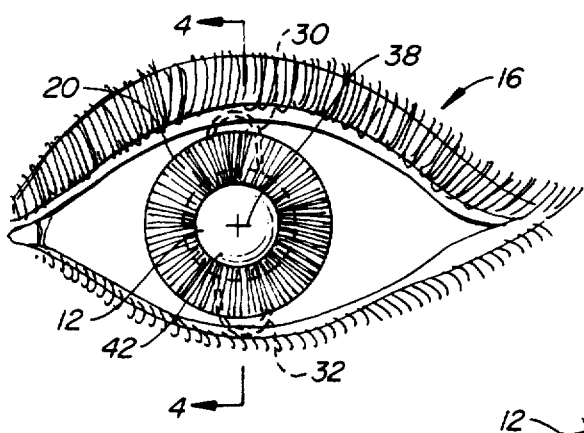
FIG._2.
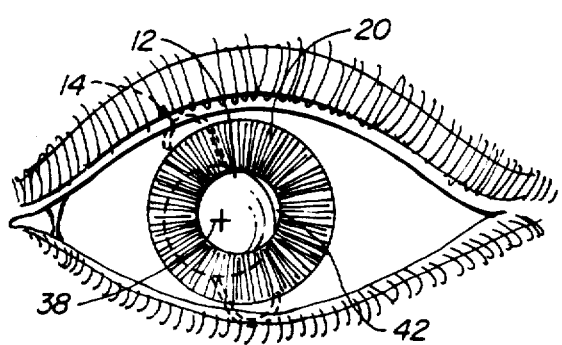
FIG._3.

INTRAOCULAR LENS APPARATUS AND METHOD FOR IMPLANTATION OF SAME

This application is a continuation-in-part of my earlier filed application Ser. No. 340,504 filed Jan. 18, 1982, now abandoned.

The present invention relates to a novel and useful intraocular lens apparatus and method for implanting an intraocular lens within the eye, especially in the posterior chamber of the eye following cataract surgery.

The implantation of intraocular lenses in the eye, and in particular the posterior chamber of the eye, has been found to be the most convenient way to correct for vision loss following cataract surgery. Implantation in the posterior chamber provides an optical advantage in that the artificial or intraocular lens is being placed at or near the location of the original natural lens. As may be apparent, the placement of an intraocular lens in the posterior chamber is more difficult than implantation in the anterior chamber of the eye since the lens must be inserted through the pupil. Also, the operation of any fixation mechanism in the posterior chamber must be effected without direct visual observation by the physican since the iris blocks most of the posterior chamber.

Implantation of lenses such as the intraocular lens disclosed in U.S. Pat. No. 4,159,546, has proved to be difficult, since the fixation obtained from the ciliary body often leaves the optical portion misaligned behind the pupil. In other words, the artifical intraocular will not perform up to its optical potential because it has been supported and fixed such that the optical zone lies partly or wholly behind the iris.

Misalignment or bad centering of the optical zone in relation to the pupil also causes focal iritis, and immune response resulting in fibrosis between the iris and capsule remnant or the intraocular lens in one of its forms. It is believed that placement of the intraocular lens in the posterior chamber away from the pupil permits the edge of the optical zone to rub the iris.

An intraocular lens solving the problem of misalignment of the optical zone in the posterior chamber of the eye would be a significant advance in the field of implantation of intraocular lenses.

SUMMARY OF THE INVENTION

In accordance with the present invention a novel and useful intraocular lens apparatus and method for implantation of the same centered in relation to the pupil is provided.

The apparatus of the present invention utilizes an optical lens portion or optical zone and means intended for holding the optical lens portion in relation to a part of the eye such as the pupil.

A marking is applied to the surface of the optical lens portion for indication of a specific zone or point of the same. The marking includes an amount of material which is substantially nonreactive to human tissue. The material may be permanently etched or otherwise fixed to the surface of the optical lens portion or may comprise a material which is substantially nonreactive to human tissue. The marking may be in any shape or form but a geometric figure has been found to be most useful. Since the pupil is normally round, a symmetrical geometric figure such as a circle, triangle, +, and the like, aids the physician in the centering or positioning of the optical lens portion in the posterior chamber of the eye. The marking may also be composed of a material which is at least slightly soluble in aqueous humor such that the marking remains on the surface of the optical lens portion for a short time during the implantation operation. Thereafter, the marking would be dissolved or otherwise removed by the aqueous humor and expelled from the eye through the trabecula in the anterior chamber or by absorption by the surface of the iris. The material may be permanently affixed to the lens surface and be visible only at the periphery of the optical lens portion of under certain lighting conditions. In either case, the marking would not interfere with the passage of light through the optical lens portion.

The invention may be deemed to include a method for implantation of an intraocular lens which includes the steps of inserting into an eye an intraocular lens having an optical lens portion with a marking applied to the surface for indication of a specific zone of the optical lens portion. The optical lens portion would then be positioned in relation to at least one part of the eye, for example, the pupil of the eye. The physician would then effect the holding of the optical lens portion in relation to the pupil.

It may be apparent that a novel and useful intraocular lens apparatus and method for implantation of the same has been described.

It is an object of the present invention to provide an intraocular lens apparatus and method for implantation of the same which permits the physician to center or align the intraocular lens within the eye, especially in the posterior chamber of the eye prior to effecting the holding mechanism for the intraocular lens.

It is another object of the present invention to provide an intraocular lens apparatus and method for implantation of the same which permits the physican to manipulate the intraocular lens in the posterior chamber of the eye although pupil constriction occurs which results in fixing of the intraocular lens optical portion directly between the pupil and the retina of the eye.

It is yet another object of the present invention to provide an intraocular lens apparatus and method for implantation of the same which reduces the possibility of focal iritis caused by misalignment of the intraocular lens within the eye.

It is still another object of the present invention to provide an intraocular lens apparatus and method for implantation of the same which employs a marking material which is nonreactive to human tissue and may be gradually removed by the normal convection currents within the aqueous humor of the eye.

Another object of the present invention is to provide an intraocular lens apparatus and method for implantation of the same which provides the physician with an instantaneous postoperative indication of misalignment of the intraocular lens within the eye.

The invention possesses other objects and advantages especially as concerns particular characteristics and feature thereof which may be apparent as the specification continues.

BRIEF DESCRIPTION OF THE DRAWINGS

FIG. 1 is a top plan view of the intraocular lens of the present invention.

FIG. 2 is a top plan view showing the intraocular lens of the present invention inserted within the posterior chamber of the eye.

FIG. 3 is a top plan view showing the intraocular lens of the present invention misaligned in the posterior chamber of the eye.

FIG. 4 is a view taken along line 4—4 of FIG. 2.

For a better understanding of the invention, reference is made to the following detailed description which should be referenced to the hereinabove described drawings.

DESCRIPTION OF THE PREFERRED EMBODIMENTS

Various aspects of the present invention will evolve from the following detailed description of the preferred embodiments thereof which should be taken in conjunction with the hereinabove described drawings.

The invention as a whole is represented in the drawings by reference character 10. The intraocular lens 10 includes an optical lens portion 12 depicted in the drawings as a plano-convex lens body. Lens portion 12 may be constructed of any suitable material such as glass, plastic, such as methyl methacrylate or other lens materials known in the art. It should be understood that lens portion 12 be suitable for implantation within the eye 20 and be nonreactive to human tissue therein. Intraocular lens 10 also includes means 14 for holding optical lens portion 12 in relation to at least a part of the eye 16, FIGS. 1 and 4. With reference to FIG. 4, it may be seen that eye 16 includes a cornea 18 and iris 20. Iris 20 forms the demarcation zone between the posterior chamber 22 and the anterior chamber 24 of the eye. The angle 26 in the anterior chamber is located at the periphery of the iris and serves as the natural drain for a aqueous humor. Ciliary body provides the support for the natural lens which has been removed from the eye.

Means 14 for holding optical lens portion 12 to a portion of the eye, in this case the ciliary body 28 found in the posterior chamber 22 of eye 16, is in the form of open loops or strands 30 and 32. With reference to U.S. Pat. No. 4,159,546, means 14 is known in the art as the Shearing support system. Means 14 is activated by placement of the optical lens portion in the posterior chamber and releasing loops 30 and 32 for placement in the ciliary body 28. Openings 34 and 36 in optical lens portion 12 provide points for permitting the physican to manipulate lens 10 with a surgical tool, specifically a rotational motion, during implantation and fixation of the lens within eye 16.

Lens 10 also includes as one of its elements a marking 38 which appears on the surface of the optical lens portion 12. Marking 38 may be etched to the surface 40 of optical lens portion 12 or formed therewithin. In any case, marking 38 must appear on the side of optical lens portion 12 associated with surface 40. Marking 38 may also be formed by applying a certain amount of material on the surface 40 of optical lens portion 12.

Where marking 38 is formed from a material applied to surface 40 of optical lens portion 12, such material must be substantially nonreactive to human tissue. In addition, the material may be slightly soluble or removed from surface 40 by aqueous humor. For example methylene blue, gentian violet and/or fluorescein may be used in this regard. The latter dye is capable of fluorescence. In other words, marking 38 in this embodiment would remain on surface 40 during the implantation operation, but would be removed by the natural convection currents in the aqueous humor at some time thereafter. The material could be finally disposed of and expelled from the eye either by absorption by the surface of iris 20 or by flowing through the natural drain found in the angle 26 of eye 16. As shown in FIGS. 1-3, marking 38 is in the form of a cross. It should be noted that marking 38 may take any form, however, symmetrical geometric figures serve quite will in aiding the physican in the placement of lens 10 within eye 16.

Turning to FIGS. 2 and 3, it may be seen that in operation the physican inserts lens 10 within the posterior chamber 22 of eye 16 by passing lens 10 through the pupil 42. Loops 30 and 32 of means 14 are placed in ciliary body 28 to hold optical lens portion 12 in place. FIG. 2 depicts optical lens portion 12 as being perfectly centered or aligned behind pupil 42. The physician is able to see this exactly in that marking 38 surrounds the very center of optical lens portion 12. Spacing the outer edge of marking 38 uniformly from iris 20 behind pupil 42 achieves this result. It has been found that the maneuvering of lens 10 causes the constriction of iris 20 rendering alignment of lens 10 in relation to pupil 42 a difficult task with prior art lenses. However, marking 38 permits the physician to observe the position of optical lens portion 12 at all times during the implantation operation. It should be noted that surface 40 of optical lens portion 12 does touch the posterior chamber side of iris 20. However, the sharp edge formed between surfaces 40 and 44 of optical lens portion 12 does not touch iris 20 when lens 12 is perfectly aligned as shown in FIG. 2. With reference to FIG. 3, it may be seen that this alignment of optical lens portion 12 is easily detected during the operation or postoperatively by the comparison of marking 38 with the periphery of pupil 42. As heretofore explained, alignment of optical lens portion 12 with pupil 42 provides the maximum correction for eye 16 after removal of the natural lens with cataract surgery. Alignment also prevents the edge between surfaces 40 and 44 from jabbing or rubbing iris 20, which may result in an immune reaction.

Although means 14 was depicted in the present embodiment as being a Shearing fixation system, many other fixation or holding means may be employed in the posterior chamber. Thus, the lens of the present invention eliminates the blind fixation of intraocular lens 10 in the posterior chamber of the eye, which heretofore has been unavoidable. The perfect alignment or centering of lens 10 also eliminates the reentering of eye 16 postoperatively to correct this condition.

While in the foregoing embodiments of the present invention have been set forth in considerable detail for the purposes of making a complete disclosure of the invention, it may be apparent to those of skill in the art that numerous changes may be made in such details without departing from the spirit and principles of the invention.

What is claimed is:

1. An intraocular lens apparatus comprising:
   a. an optical lens portion;
   b. means intended for holding said optical lens portion in relation to at least a part of an eye;
   c. a marking appearing on the optical lens portion for indication of a specific zone of said optical lens portion, said marking comprising a material applied to said optical lens portion which is substantially non-reactive to human tissue.

2. The intraocular lens apparatus of claim 1 in which said material is fluorescent.

3. The intraocular lens apparatus of claim 1 in which said marking is in the form of a geometric figure.

4. The intraocular lens apparatus of claim 3 in which said geometric figure is symmetrical.

5. The intraocular lens apparatus of claim 1 in which said amount of material comprising said marking is soluble in aqueous humor.

6. A method for implantation of an intraocular lens comprising the steps of:
   a. inserting into an eye an intraocular lens having an optical lens portion and means for holding said optical lens portion in relation to at least a portion of an eye said optical lens portion having a marking applied thereto for indication of a specific zone of said optical lens portion, said marking comprising a material applied to said optical lens portion, which is substantially non-reactive to human tissue;
   b. positioning said optical lens portion in relation to at least a part of the eye; and
   c. effecting the holding of said optical lens portion by said means for holding said lens portion in relation to at least a part of the eye.

7. The method of claim 6 in which said material comprising said marking is soluble in aqueous humor.

8. The method of claim 6 in which said material comprising said marking is flourescent.

* * * * *